United States Patent [19]

Naegeli

[11] 4,072,719

[45] Feb. 7, 1978

[54] 4-(2,6,6-TRIMETHYL-2-CYCLOHEXEN-1-YLIDENE)-BUTAN-2-OL

[75] Inventor: Peter Naegeli, Wettingen, Switzerland

[73] Assignee: Givaudan Corporation, Clifton, N.J.

[21] Appl. No.: 733,724

[22] Filed: Oct. 19, 1976

Related U.S. Application Data

[62] Division of Ser. No. 664,212, March 5, 1976, Pat. No. 4,011,245.

[30] Foreign Application Priority Data

Mar. 11, 1975 Switzerland ........................ 3053/75
Dec. 30, 1975 Switzerland ...................... 16871/75

[51] Int. Cl.$^2$ ...................... C07C 33/05; C07C 33/02

[52] U.S. Cl. ........................... 260/617 A; 131/17 R; 260/347.8; 260/617 R; 252/522; 426/537; 426/650; 426/660; 560/260

[58] Field of Search ........................ 260/617 R, 617 A

[56] References Cited

U.S. PATENT DOCUMENTS

| 778,243 | 12/1904 | Hofmann | 260/617 A |
|---|---|---|---|
| 3,162,682 | 12/1964 | Shotts et al. | 260/617 C |
| 3,899,597 | 8/1975 | Mookheyie et al. | 260/617 A |
| 3,932,485 | 1/1976 | Surmatis | 260/617 A |

Primary Examiner—Norman Morgenstern
Attorney, Agent, or Firm—Thomas Cifelli, Jr.; Robert F. Tavares

[57] ABSTRACT

Theaspiran is a novel fragrance and flavor substance. Its uses and novel process for making it are disclosed.

1 Claim, No Drawings

4-(2,6,6-TRIMETHYL-2-CYCLOHEXEN-1-YLIDENE)-BUTAN-2-OL

This is a division, of application Ser. No. 664,212 filed Mar. 5, 1976, now U.S. Pat. No. 4,011,245.

FIELD OF THE INVENTION

This invention relates to the fragrance and flavor fields.

SUMMARY OF THE INVENTION

Theaspiran (2,6,10,10-tetramethyl-1-oxaspiro[4,5]-dec-6-ene) of formula IV given in the following Formula Scheme is a known compound disclosed in Tetrahedron Letters 1995 (1969). It has now been found in accordance with the present invention that this compound has special organoleptic properties on the basis of which it is particularly suitable as an odor-and/or flavor-imparting substance.

Theaspiran can be detected in extremely slight concentrations in various essential oils, for example in raspberry oil or in the oil of the yellow passion fruit [see Helv. Chim. Acta 57, 1301 (1974); 55, 1916 (1972); 54, 1881 (1971)]. Nevertheless, the finding that theaspiran is well suited as an odor- and/or flavor-imparting substance must be considered to be surprising since none of these publications contains any reference to the special organoleptic properties of theaspiran.

DESCRIPTION OF THE PREFERRED EMBODIMENTS

The invention is accordingly concerned in one of its aspects with odorant and/or flavouring compositions which contain as the essential odour- and/or flavour-imparting ingredient theaspiran in practically pure form or in the form of mixtures (with the exception of natural mixtures containing theaspiran).

By practically pure theaspiran there should be understood, in particular, theaspiran which is free from the accompanying substances which are present in addition to theaspiran in the said natural extracts. As practically pure theaspiran in the scope of the present invention, there should also be understood, for example, synthetically prepared theaspiran.

The theaspiran used in accordance with the invention as an odour- and/or flavour-imparting substance is distinguished by special fresh, fruity odour or flavour properties. Of particular interest is a berry-like, green note and a sweetish, woody nuance appearing with increasing concentration. The theaspiran can accordingly be used, for example, for the perfuming or flavoring of products such as cosmetics (soaps, salves, powders etc), detergents, foods, luxury goods and drinks, the theaspiran preferably not being used alone but in the form of compositions which also contain other odour- or flavour-imparting substances.

In another of its aspects, the invention is concerned with a process for the manufacture of the odorant and/or flavouring compositions aforesaid, which process comprises adding theaspiran in practically pure form or in the form of mixtures (with the exception of natural mixtures containing theaspiran) to known odorant and/or flavouring substance compositions or mixing theaspiran in practically pure form or in the form of mixtures (with the exception of natural mixtures containing theaspiran) with natural or synthetic compounds or mixtures thereof suitable as ingredients of odorant and/or flavouring substance compositions.

Because of its very natural notes, theaspiran is especially suited as an odorant for modifying known compositions; for example, those of the Chypre type. Thus, for example, it is very well suited to combination with flower notes such as, for example, neroli and rose notes.

The concentration of theaspiran in the present compositions can vary within wide limits depending on the purpose of use; for example, between about 1 wt.% (detergents) and about 15 wt.% (alcoholic solutions). In perfume bases or concentrates, the concentrations can of course also be higher.

As a flavour-imparting substance, theaspiran can be used, for example, for the production or improvement, intensification, enhancement or modification of fruit or berry (e.g. raspberry, strawberry, apricot, citrus fruit, pear etc.) flavors in foods (yoghurt, confectionery etc), in luxury goods (tobacco etc) and in drinks (lemonades etc).

The pronounced flavour qualities of practically pure, especially synthetically prepared theaspiran, enables it to be used in low concentrations. A suitable amount lies in the range of 0.00001-1 ppm, preferably 0.001-0.1 ppm, in the finished product, namely the aromatised food, luxury goods or drink.

Theaspirane may be added as such or in the form of flavouring agents to the products to be aromatized. In the latter case the flavouring agent can naturally contain other flavouring ingredients, especially those customarily used for the various purposes listed on page 4.

The manufacture of odorant or flavourant compositions containing theaspiran can be effected in a manner known per se, see for example Perfume and Flavour Chemicals, S. Arctander, Montclair 1969, Perfume and Flavour Chemicals of Natural Origin, S. Arctander, 1960, Food Flavourings, Composition, Manufacture and Use, 2nd. ed., J. Merory, Westport 1968. Thus, flavouring agents may contain e.g. from 0.01 ppm-5‰ of theaspiran.

Some effects which can be produced with theaspiran are compiled in the following Table.

Table

| Aroma | Amount | Effect |
|---|---|---|
| Tobacco (Top flavour) | 0.0005 ppm in the finished product | Better tenacity aroma; intensified fruitier impression. |
| Vanilla | 0.03 ppm in the finished product | Rounding-off effect; woody nuance. |
| Raspberry | 0.001 ppm in the finished product | Rounding-off effect; pleasant, woody natural nuance. |

Theaspiran can be mixed with the ingredients used for flavouring substance compositions or added to such flavorants in the usual manner. By the flavorants used in accordance with the present invention there are to be understood flavouring substance compositions which can be diluted or dispersed in edible materials in a manner known per se. They can be converted according to methods known per se into the usual forms of use such as solutions, pastes or powders. The products can be spray-dried, vacuum-dried or lyophilised.

In the production of the aforementioned usual forms of use, the following carrier materials, thickening agents, flavour-improvers, spices, auxiliary ingredients and the like may, for example, be mentioned:

Gum arabic, tragacanth, salts or brewer's yeast, alginates, carrageens or similar absorbants, indoles, maltol, dienals, spice oleoresins, smoke flavors, cloves, diacetyl, sodium citrate, monosodium glutamate, disodium inosine-5'-monophosphate (IMP), disodium guanosine-5-phosphate (GMP), special flavor-imparting substances, water, ethanol, propylene glycol and glycerine.

From the foregoing it will be appreciated that the invention also includes within its scope a method of imparting an odour and/or a flavour to materials by applying thereto or incorporating therein an odorant and/or flavouring composition as hereinbefore defined or theaspiran in practically pure form or in the form of mixtures (with the exception of natural mixtures containing theaspiran).

The present invention is also concerned with a novel improved process for the manufacture of theaspiran, which process comprises treating 4-(2,6,6-trimethyl-2-cyclohexen-1-ylidene)-butan-2-ol of formula III in the following Formula Scheme with an acid.

Especially suitable acids are protonic acids such as inorganic and organic protonic acids (e.g. sulphuric acid, phosphoric acid, p-toluenesulphonic acid etc) or Lewis acids (e.g. $BF_3$, $SnCl_4$, $ZnCl_2$, etc). p-Toluenesulphonic acid is the preferred protonic acid.

The cyclization of 4-(2,6,6-trimethyl-2-cyclohexon-1-ylidene)-butan-2-ol of formula II to theaspiran of formula IV can be carried out in the presence or absence of a solvent. Suitable solvents are inert solvents such as hexane, benzene, nitromethane, chlorinated hydrocarbons (e.g. chloroform etc) and ethers (e.g. dioxane etc). Benzene and toluene are the preferred solvents. The temperature is not critical; the treatment can be carried out at room temperature or at a higher or lower temperature.

Since it is known that theaspiran can be oxidised to the flavour-imparting substance theaspirone of formula V in the following Formula Scheme (see, for example, U.S. Pat. No. 3,645,755), the process provided by the present invention also provides an advantageous access to theaspirone. The preparation of theaspirone by oxidising theaspiran (prepared according to the foregoing process) in accordance with methods known per se also forms part of this invention.

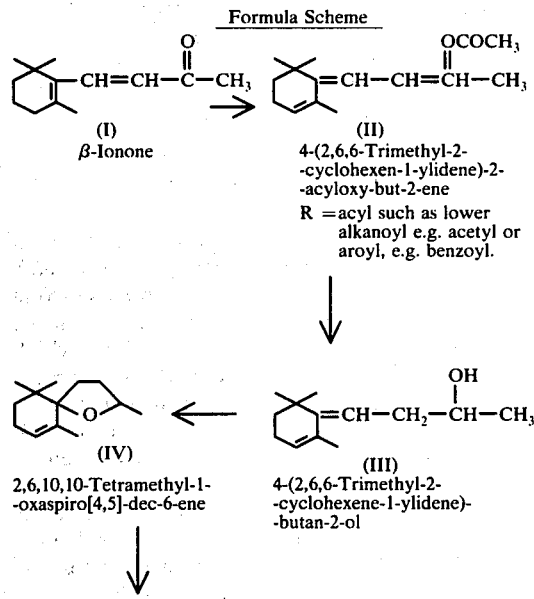

Formula Scheme (I) β-Ionone (II) 4-(2,6,6-Trimethyl-2-cyclohexen-1-ylidene)-2-acyloxy-but-2-ene
R = acyl such as lower alkanoyl e.g. acetyl or aroyl, e.g. benzoyl.

(III) 4-(2,6,6-Trimethyl-2-cyclohexene-1-ylidene)-butan-2-ol (IV) 2,6,10,10-Tetramethyl-1-oxaspiro[4,5]-dec-6-ene

(V) 2,6,10,10-Tetramethyl-1-oxaspiro[4,5]-dec-6-en-8-one

Having regard to the foregoing Formula Scheme, the alcohol of formula III can be obtained from an acyloxy compound of formula II which, in turn, can be obtained from β-ionone of formula I. An acyloxy compound of formula II can be converted into the alcohol of formula III using, for example, a complex hydride such as lithium borohydride, sodium borohydride, potassium borohydride, lithium aluminium hydride etc. The reaction is expediently carried out in an alcohol, for example an alkanol, an alcohol/ether mixture or an ether as the solvent. The temperature at which the reaction is carried out is not critical. It is, however, preferred to carry out the reaction at a temperature of ca $-10°$ C to $80°$ C.

An acyloxy compound of formula II can be obtained by reacting β-ionone of formula I with an enol acylate. Suitable enol acylates are isopropenyl acetate, isobutenyl acetate etc. The formation of an acyloxy compound of formula II is expediently carried out in the presence of catalytic amounts of acids (e.g. one of the aforementioned acids). p-Toluenesulphonic acid is the preferred acid. The enol acylate is expediently used in excess, whereby it also serves as the solvent. The reaction is preferably carried out at the reflux temperature of the reaction mixture and the ketone (acetone in the case of isopropenyl acetate) formed during the reaction is continuously removed by distillation.

It will be appreciated that formulae II and III include the four possible stereoisomers. Likewise, formulae IV and V include both diastereomeric compounds (i.e. both enantiomeric pairs).

The following Examples illustrate the present invention:

EXAMPLE 1

96 g of β-ionone are dissolved in 500 ml of isopropenyl acetate and treated with 0.6 g of p-toluenesulphonic acid monohydrate. The mixture is stirred at reflux temperature under an inert gas atmosphere for 24 hours. The excess isopropenyl acetate is distilled off from the mixture under a vacuum (temperature $\leq 50°$) and then the mixture is treated several times with hexane in order to liberate residual amounts of isopropenyl acetate and concentrated again. In this manner, there are obtained 108 g of brown-red 4-(2,6,6-trimethyl-2-cyclohexen-1-ylidene)-2-acetoxy-but-2-ene (formula II; R = acetyl).

UV (ethanol): $\lambda_{max} = 279$ nm, log $\epsilon = 4, 265$.

IR (film): 1755, 1650, 1580, 1370, 1220/1205, 1150/1140, 1040, 1020, 945, 925, 885/875/865, 818 $cm^{-1}$.

NMR ($CDCl_3$ + TMS): $\delta = 6.65 - 5.85$ (2H, m); $\delta = 5.78$ (1H, broad t); $\delta = 2.20$ and $2.15$ (3H, each S); $\delta = 2.05$ (3H, broad S); $\delta = 1.85$ (3S, narrow m); $\delta = 1.28$ ppm (6H, S).

MS: m/e: 234, fragments at 192, 177, 159, 149, 136, 121, 107, 91, 81, 77, 71, 65, 55, 43 = base peak.

The resulting crude acetoxy compound of formula II (108 g) is dissolved in 400 ml of ethanol (96%) and added dropwise within 10 minutes at $20°-30°$ C with slight cooling to a suspension of 20 g of sodium borohydride in 600 ml of 96% ethanol. The mixture is then heated until a slight reflux occurs and stirred at this temperature for 15 minutes. The end of the reaction can be detected by a spontaneous colour change from dark-yellow to lemon-yellow. After cooling to room temperature, the cloudy mixture is poured on to saturated ammonium chloride solution/ice and the mixture is extracted with hexane. After the usual washing to neutrality with water and drying over anhydrous sodium sulphate, the solvent is evaporated under a vacuum. There are obtained 96 g of crude 4-(2,6,6-trimethyl-2-cyclohexen-1-ylidene)-butan-2-ol (formula III).

UV (ethanol): $\lambda_{max}$: 239 nm (log $\epsilon$ = 4).

IR (film): 3300, 1380/1370/1360, 1125, 1085, 95), 880, 830 cm$^{-1}$.

NMR (CDCl$_3$ + TMS): $\delta$ = 5.7 (1H, broad t); $\delta$ = 5.4 (1H, t with J = 7 Hz); $\delta$ = 3.9 (1H, m with J = 6Hz); $\delta$ = 2.55 (2H, broad t with J = 7 Hz); $\delta$ = 1.85 (3H, narrow m); $\delta$ = 1.25 (3H, d with J = 6Hz); $\delta$ = 1.23 ppm (6H, S).

MS: m/e: 194, fragments at 189, 161, 150, 135 = base, 121, 107, 93, 79, 69, 55, 45, 41.

96 g of the crude alcohol of formula III are heated to reflux in 1.3 liters of absolute benzene in the presence of 1 g of p-toluenesulphonic acid monohydrate for 10 hours. The solution is poured on to a cold saturated bicarbonate solution and extracted with hexane. After washing to neutrality and drying the extract over sodium sulphate, the solvent is evaporated in vacuo. The resulting 96 g of brown oily crude theaspiran of formula IV are separated from the first runnings and residue by short-path distillation. Yield:

77 g of theaspiran of formula IV; boiling point = 75° C/0.2 mm Hg; n$_D^{20}$ = 1.492.

IR (film): 1475, 1455, 1380, 1360, 1285, 1195, 1160/1150, 1130, 1110/1085, 1080/1060, 1040, 1005, 990, 975, 930, 910/900, 880, 825, 775, 725 cm$^{-1}$.

NMR (CDCl$_3$ + TMS): Isomer A $\delta$ = 5.25 (1H, narrow m); $\delta$ = 4.1 (1H, broad m); $\delta$ = 1.75 (3H, narrow m); $\delta$ = 1.26 (3H, d with J = 6Hz); $\delta$ = 0.95 and 0.88 ppm (each 3H, s).

Isomer B $\delta$ = 5.40 (1H, narrow m); $\delta$ = 4.05 (1H, broad m); $\delta$ = 1.7 (3H, narrow m); $\delta$ = 1.28 (3H, d with J = 6Hz); $\delta$ = 1.00 and 0.88 ppm (each 3H, s).

MS: m/e: 194, fragments at 179, 151, 135 = base peak, 123, 109, 96, 82, 77, 67, 55, 41.

EXAMPLE 2

5.7 g (30 mmol) of theaspiran are dissolved in 60 ml of anhydrous tert.butanol and treated within 2 hours at 40° C with 120 ml (ca 30 mmol of CrO$_3$) of tert.butylchromate solution [150 g of CrO$_3$, 400 ml of tert.butanol, 140 ml of acetic anhydride]. The mixture is then stirred at 40° C. A further 20 ml of tert.butylchromate solution are added dropwise after 8 days and the same amount is added after 10 days. After a total of 16 days, the mixture is worked-up. The mixture is taken up in 1 liter of methylene chloride, covered with ice and stirred for 1 hour with 1 litre of sulphite/bisulphite solution [40 g of sodium bisulphite, 50 g of sodium sulphite, 1 liter of water]. The mixture is subsequently washed neutral with saturated sodium bicarbonate solution and water, dried over magnesium sulphate and evaporated to dryness. There are obtained 3.0 g of a yellow oil which is purified by column chromatography in a 30-fold amount of silica gel (particle size 0.063–0.200 mm) using hexane/ether mixtures containing 5–10% ether. The yield is 20% of theaspirone of boiling point 88° C/0.12 mm Hg.

UV (ethanol): $\lambda_{max}$ = 235 nm ($\epsilon$ = 11740).

MS: m/e: 208 = M+, 193, 175, 152, 110, 96, 82, 69, 55, 41.

IR (film): 1675, 1630, 1480, 1450, 1390/80/70, 1345, 1310, 1280, 1270, 1160, 1090, 980, 920, 890 cm$^{-1}$.

NMR (CDCl$_3$ + TMS): 1H at $\delta$ = 5.72 (narrow quadruplet with J = 1.5 H$_2$); 1H at $\delta$ = 4.2° centred (multiplet); 3H at $\delta$ = 2.01 and $\delta$ = 1.99 (each singlet for the two diastereomers); 3H at $\delta$ = 1.30 (doublet with J = 6Hz); 6H at $\delta$ = 0.99 and 1.02 (singlet for the gem dimethyl groups).

EXAMPLE 3

| Tobacco flavour (Top Flavour) | Parts by weight | |
|---|---|---|
| | A | B |
| Methylcyclopentenolone | 2.0 | 2.0 |
| Ethyl acetate | 2.0 | 2.0 |
| Ethyl anisate | 4.0 | 4.0 |
| Butyl formate | 4.0 | 4.0 |
| Cinnamaldehyde | 7.0 | 7.0 |
| Capric aldehyde (10% in ethanol) | 10.0 | 10.0 |
| Vanillin | 10.0 | 10.0 |
| Amyl salicylate | 10.0 | 10.0 |
| C$_{14}$-Aldehyde (10% in ethanol) | 10.0 | 10.0 |
| Ethylvanillin | 20.0 | 20.0 |
| Heliotropin | 20.0 | 20.0 |
| Propyl acetate | 25.0 | 25.0 |
| Amyl formate | 25.0 | 25.0 |
| Isoamyl acetate | 25.0 | 25.0 |
| Coumarin | 60.0 | 60.0 |
| Ethyl butyrate | 75.0 | 75.0 |
| Benzaldehyde | 110.0 | 110.0 |
| Benzyl benzoate | 250.0 | 250.0 |
| Theaspiran | — | 5.0 |
| Ethanol | 331.0 | 326.0 |
| | 1000.0 | 1000.0 |

Composition B has a much fruitier aroma compared with composition A and persists substantially longer than composition A.

A 10% ethanolic solution of this top flavour is sprayed onto fresh cut tobacco, e.g. 2–10 g of the 10% solution onto 50 g of tobacco.

EXAMPLE 4

| Vanilla flavour | Parts by weight | |
|---|---|---|
| | A | B |
| Guaiacol (1% in ethanol) | 1.0 | 1.0 |
| Heliotropin (1% in ethanol) | 1.0 | 1.0 |
| Isoeugenol (1% in ethanol) | 2.0 | 2.0 |
| p-Hydroxybenzaldehyde (1% in ethanol) | 3.0 | 3.0 |
| Vanillin | 20.0 | 20.0 |
| Ethylvanillin | 120.0 | 120.0 |
| Theaspiran (1% in ethanol) | — | 3.0 |
| Ethanol | 853.0 | 850.0 |
| | 1000.0 | 1000.0 |

Composition B differs organoleptically in a very advantageous manner from the composition A which is a conventional vanilla aroma. In particular, the theaspiran imparts a weakly woody and fruity note, by which means the vanilla fragrance is rounded off in a remarkable manner.

100 g of the above vanilla flavour are incorporated (using methods known per se) into 100 kg of caramel (milk/cream) toffees.

EXAMPLE 5

| Raspberry flavour | Parts by weight A | B |
|---|---|---|
| Leaf alcohol | 1 | 1 |
| Heliotropin | 1 | 1 |
| Maltol | 2 | 2 |
| Bergamotte oil | 3 | 3 |
| Citral | 12 | 12 |
| Diethyl succinate | 13 | 13 |
| $C_{14}$-Aldehyde | 15 | 15 |
| Jasmin absolute | 15 | 15 |
| Celery oil | 16 | 16 |
| Anethole | 21 | 21 |
| Ethyl valerate | 21 | 21 |
| Methyl anthranilate | 22 | 22 |
| Yara-Yara | 26 | 26 |
| $C_{16}$-Aldehyde | 30 | 30 |
| Cinnamic alcohol | 36 | 36 |
| Vanillin | 40 | 40 |
| Indole | 38 | 38 |
| Ethyl acetate | 58 | 58 |
| β-Ionone | 630 | 630 |
| Theaspiran (1% in ethanol) | — | 10 |
|  | 1000 | 1000 |

Composition B has a substantially more rounded-off action, is less obtrusively sweet and is more natural than composition A. The composition B provides a very pleasant, woody undertone.

100 g of the above flavour composition are incorporated into 100 kg of hard boild sweets (hard candy), using methods known per se.

EXAMPLE 6

| Pear flavour | Parts by weight A | B |
|---|---|---|
| Eugenol | 1.0 | 1.0 |
| Geraniol | 1.0 | 1.0 |
| Maltol | 1.0 | 1.0 |
| Anethole (10% in ethanol) | 2.0 | 2.0 |
| Vanillin | 2.0 | 2.0 |
| Piperonyl acetate | 2.5 | 2.5 |
| Geranyl propionate | 5.0 | 5.0 |
| Linalyl acetate | 10.0 | 10.0 |
| Amyl acetate | 100.0 | 100.0 |
| Ethanol | 875.5 | 875.5 |
| Theaspiran | — | 5 |
|  | 1000.0 | 1005.0 |

Composition B has a substantially rounder and fresher action than the composition A. Further, a pleasant woody undertone can also be detected in composition B.

50 g of the above flavour composition are used to aromatize 100 kg of jelly, using methods known per se.

EXAMPLE 7

| Composition (Fougere) | Parts by weight |
|---|---|
| Bergamotte oil | 200 |
| Amyl salicylate | 150 |
| Coumarin | 100 |
| Rhodinol extra | 50 |
| Linalool | 50 |
| Phenylethyl alcohol | 30 |
| Citronellol | 30 |
| Tree moss absolute (50% in ethyl phthalate) | 20 |
| Patchouli oil | 20 |
| Eugenol | 10 |
| Lilial | 40 |
| Linalyl acetate | 100 |
| Alcohol 95° | 150 |
| Theaspiran (10% in ethyl phthalate) | 50 |
|  | 1000 |

By the addition of theaspiran, a very original Fougere composition can be produced from an initially conventional Chypre composition; especially remarkable is the aromatic fragrance reminiscent of woodland soil.

EXAMPLE 8

| Composition | Parts by weight |
|---|---|
| Petitgrain oil Paraguay | 400 |
| Geraniol extra | 200 |
| Phenylethyl alcohol | 160 |
| Methyl anthranilate | 160 |
| p-Methylquinoline (10% in ethanol) | 10 |
| Theaspiran (10% in diethyl phthalate) | 70 |
|  | 1000 |

The initially slightly original flowery composition (neroli) has a substantially more rounded-off action and is fuller, softer and sweeter by the addition of theaspiran. The impression of a fresh, natural blossom fragrance is striking.

What is claimed is:
1. 4-(2,6,6-Trimethyl-2-cyclohexen-1-ylidene)-butan-2-ol.

* * * * *